United States Patent
Wilson et al.

(10) Patent No.: US 7,175,631 B2
(45) Date of Patent: Feb. 13, 2007

(54) RADIOLUCENT AIMING GUIDE

(75) Inventors: Frank A. Wilson, Essington, PA (US); Mark E. Nadzadi, Iowa City, IA (US)

(73) Assignee: Synthes (U.S.A.), West Chester, PA (US)

( * ) Notice: Subject to any disclaimer, the term of this patent is extended or adjusted under 35 U.S.C. 154(b) by 440 days.

(21) Appl. No.: 10/724,875

(22) Filed: Dec. 2, 2003

(65) Prior Publication Data

US 2004/0167533 A1    Aug. 26, 2004

Related U.S. Application Data

(63) Continuation of application No. 09/577,982, filed on May 25, 2000, now Pat. No. 6,656,189.

(51) Int. Cl.
    *A61B 17/90* (2006.01)
(52) U.S. Cl. ........................................................ 606/97
(58) Field of Classification Search ................ 606/95, 606/96, 97, 98, 64, 62, 80, 87; 604/529
    See application file for complete search history.

(56) References Cited

U.S. PATENT DOCUMENTS

| | | | |
|---|---|---|---|
| 2,531,734 A | 11/1950 | Hopkins | 128/83 |
| 3,613,684 A | 10/1971 | Sheridan | 128/347 |
| 3,704,707 A | 12/1972 | Halloran | 128/92 EB |
| 4,037,592 A | 7/1977 | Kronner | 128/92 EB |
| 4,418,422 A | 11/1983 | Richter et al. | 378/205 |
| 4,541,424 A | 9/1985 | Grosse et al. | 129/92 EB |
| 4,621,628 A | 11/1986 | Brudermann | 128/92 VD |
| 4,625,718 A | 12/1986 | Olerud et al. | 128/92 VD |
| 4,722,336 A | 2/1988 | Kim et al. | 128/303 B |
| 4,803,976 A | 2/1989 | Frigg et al. | 33/286 |
| 4,848,327 A | 7/1989 | Perdue | 128/92 R |

(Continued)

FOREIGN PATENT DOCUMENTS

EP   0 923 906 A2   6/1999

(Continued)

OTHER PUBLICATIONS

M.E. Müller et al., *Manual of Internal Fixation* at 346-353 (3rd Ed. 1995).

*Primary Examiner*—Cary E. O'Connor
(74) *Attorney, Agent, or Firm*—Jones Day

(57) ABSTRACT

The present invention is directed to a radiolucent aiming guide for locating and drilling through the holes in the distal end of an implanted intramedullary nail. The aiming guide comprises an elongate handle constructed substantially of a radiolucent material, which does not cast a strong image on a monitor when exposed to radiation. The radiolucent handle is used in conjunction with a protection sleeve, trocar, drill sleeve, and drill bit, which are used to locate and drill through the hole in the nail. Radiopaque components in the distal end of the protection sleeve, trocar, and drill bit are used to align the drill over the nail hole. A pair of radiopaque pins, located within the handle and lying parallel to its longitudinal axis, aid in ensuring the proper rotational alignment of the aiming guide over the nail hole. The aiming guide may also include a structure to facilitate its alignment over a second hole in the distal end of the intramedullary nail.

9 Claims, 4 Drawing Sheets

U.S. PATENT DOCUMENTS

| | | | |
|---|---|---|---|
| 4,850,344 A | 7/1989 | Olerud et al. | 128/92 VD |
| 4,865,025 A | 9/1989 | Buzzi et al. | 128/92 VD |
| 4,877,019 A | 10/1989 | Vives | 128/92 YK |
| 4,881,535 A | 11/1989 | Sohngen | 606/98 |
| 4,917,111 A | 4/1990 | Pennig et al. | 606/97 |
| 4,969,889 A | 11/1990 | Grieg | 606/97 |
| 4,976,713 A | 12/1990 | Landanger et al. | 606/62 |
| 5,013,317 A | 5/1991 | Cole et al. | 606/96 |
| 5,031,203 A | 7/1991 | Trecha | 378/205 |
| 5,070,861 A | 12/1991 | Einars et al. | 128/24 |
| 5,112,336 A | 5/1992 | Krevolin et al. | 606/96 |
| 5,127,913 A | 7/1992 | Thomas, Jr. | 606/92 |
| 5,234,434 A | 8/1993 | Goble et al. | 606/96 |
| 5,283,808 A | 2/1994 | Cramer et al. | 378/206 |
| 5,334,192 A | 8/1994 | Behrens | 606/96 |
| 5,352,228 A | 10/1994 | Kummer et al. | 606/64 |
| 5,403,321 A | 4/1995 | DiMarco | 606/96 |
| 5,411,503 A | 5/1995 | Hollstien et al. | 606/86 |
| 5,417,688 A | 5/1995 | Elstrom et al. | 606/64 |
| 5,426,687 A | 6/1995 | Goodall et al. | 378/206 |
| 5,433,720 A | 7/1995 | Faccioli et al. | 606/87 |
| 5,478,329 A | 12/1995 | Ternamian | 604/204 |
| 5,478,343 A | 12/1995 | Ritter | 606/97 |
| 5,513,240 A | 4/1996 | Hausmann et al. | 378/170 |
| 5,514,145 A | 5/1996 | Durham et al. | 606/96 |
| 5,540,691 A | 7/1996 | Elstrom et al. | 606/64 |
| 5,584,838 A | 12/1996 | Rona et al. | 606/96 |
| 5,620,449 A | 4/1997 | Faccioli et al. | 606/98 |
| 5,630,805 A | 5/1997 | Ternamian | 604/158 |
| 5,665,086 A | 9/1997 | Itoman et al. | 606/64 |
| 5,707,375 A | 1/1998 | Durham et al. | 606/98 |
| 5,722,978 A | 3/1998 | Jenkins et al. | 606/79 |
| 5,728,128 A | 3/1998 | Crickenberger et al. | 606/97 |
| 5,766,179 A | 6/1998 | Faccioli et al. | 606/98 |
| 5,772,594 A | 6/1998 | Barrick | 600/407 |
| 5,891,158 A | 4/1999 | Manwaring et al. | 606/130 |
| 6,036,657 A | 3/2000 | Millliman et al. | 600/564 |
| 6,036,696 A | 3/2000 | Lambrecht et al. | 606/97 |
| 6,129,729 A | 10/2000 | Snyder | 606/72 |
| 6,214,013 B1 | 4/2001 | Lambrecht et al. | 606/96 |
| 6,371,959 B1 | 4/2002 | Trice | 606/97 |

FOREIGN PATENT DOCUMENTS

| | | |
|---|---|---|
| WO | WO 95/30378 | 11/1995 |

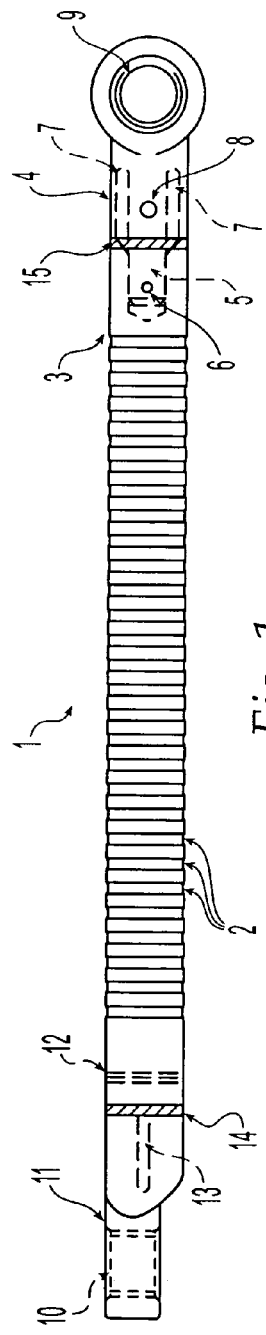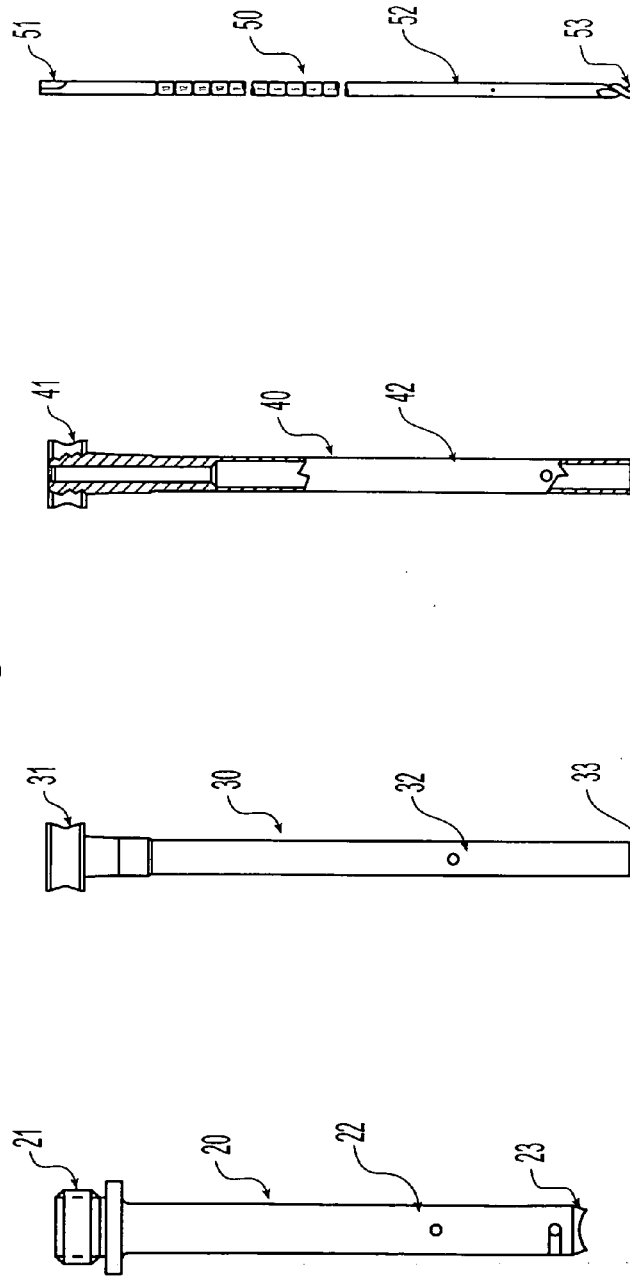

RADIOLUCENT AIMING GUIDE

CROSS REFERENCE TO RELATED APPLICATIONS

This application is a continuation of U.S. patent application Ser. No. 09/577,982 filed on May 25, 2000, now having issued as U.S. Pat. No. 6,656,189, the entire contents of which are expressly incorporated herein by reference.

FIELD OF INVENTION

The present invention relates to an aiming guide for use with an X-ray or other radiation source for accurately positioning a trocar or drill over the holes in the distal end of an implanted intramedullary nail and drilling through such holes and the surrounding bone material.

BACKGROUND OF INVENTION

Intramedullary nails are used to aid in the healing of fractured bones. A nail is implanted in the medullary canal of the bone across the fracture site in order to position the bone fragments and provide load-bearing support so that the patient can move about while the bone is healing. The nail is secured to the bone by a series of locking screws or fixation bolts, which must pass through holes in the nail and into the surrounding bone material.

After the nail is inserted into the medullary canal, the distal end of the nail is no longer visible to the eye. The nail can be viewed with the use of an X-ray or other radiation source because it is constructed of stainless steel or other radiopaque material. The nail will cast a dark, elongate image on the X-ray monitor, while the nail holes will appear as light circles or ovals. In particular, a nail hole will appear as a circle when the X-ray source is positioned such that the X-ray beam is parallel to the axis of the nail hole.

In order to secure the nail to the bone, a trocar or scalpel is used to make an incision through the soft tissue to the bone material, and a drill is used to drill through the nail hole and surrounding bone material for insertion of the locking screw. An aiming guide is used with the X-ray source in order to accurately position the trocar and surgical drill over the nail holes.

Various aiming guides are already known in the art, such as those disclosed in U.S. Pat. Nos. 4,969,889, 4,917,111, and 5,478,343. In general, each of those devices has a handle portion constructed of a radiolucent material, such as plastic, which is relatively invisible to X-rays and thus will not cast a strong image on the X-ray monitor. Certain radiopaque aiming components, such as metal rings or other structures, are attached to or located within the distal end of the radiolucent handle. The radiopaque components will cast a definite image on the X-ray monitor when the X-ray source is turned on. The aiming guide is then positioned over the nail in such a manner that the image(s) cast by the radiopaque aiming components is (are) superimposed over the circular image of the nail hole on the X-ray monitor. Once the aiming guide is properly positioned over the nail hole, a trocar is used to make an incision to the surface of the bone above the nail hole, and a drill can be used to drill accurately through the nail hole and surrounding bone material for insertion of the locking screws.

Certain aiming guides, such as that disclosed in U.S. Pat. No. 4,969,889, contain substantial radiopaque components and thus tend to be rather heavy and bulky. Other aiming guides, such as that disclosed in U.S. Pat. No. 5,478,343, require the simultaneous manipulation of more than one instrument in order to locate and drill through the nail hole. Also, the protection sleeves and trocars used in the prior art were constructed entirely or substantially of metal, which made them heavy and tended to obstruct the view on the X-ray monitor. A more compact, unitary, and lighter weight aiming guide having fewer radiopaque components would prove advantageous.

SUMMARY OF THE INVENTION

The present invention is a radiolucent aiming guide that is used with an X-ray source to accurately position a trocar or drill over a nail hole in order to make the incision and hole for insertion of a locking screw. The aiming guide has an elongate handle constructed of a radiolucent material to place the surgeon's hands at a distance away from the area of the X-ray beam. A threaded hole, running perpendicular to the longitudinal axis of the handle, is located at each end of the handle. A hollow, cylindrical protection sleeve is screwed into one of the threaded holes in the handle. A protection sleeve is constructed substantially of a radiolucent material, with the exception of the tip at its distal end, which is made of metal or another radiopaque material that casts a dark image on the X-ray monitor. A trocar is inserted into the protection sleeve for making the incision to the bone. The trocar is constructed substantially of a radiolucent material except for the solid pointed tip at its distal end, which is constructed of metal or another radiopaque material. The radiopaque tip of the trocar will cast a dark image within the image cast by the radiopaque tip of the protection sleeve.

The aiming guide is positioned over the limb such that the longitudinal axes of the trocar and protection sleeve are aligned parallel to the direction of the X-ray beam. When the aiming guide is positioned in that fashion, the radiopaque tips at the distal ends of the protection sleeve and trocar will cast concentric circular images on the X-ray monitor. The aiming guide is moved until those concentric circular images are superimposed over the circular image of the nail hole, which indicates that the protection sleeve and trocar are in alignment with the nail hole.

The proper rotational alignment of the aiming guide with respect to the nail hole is checked by means of two radiopaque pins, which lie parallel to and on either side of the longitudinal axis of the handle near the threaded hole. Those two pins cast dark images on the X-ray monitor on either side of the image of the nail when the aiming guide is properly oriented with respect to the nail. Once the aiming guide is accurately oriented over the nail hole, the trocar is used to remove the soft tissue lying above the nail hole.

After the soft tissue has been scraped away, the trocar is withdrawn and replaced with a hollow, essentially cylindrical drill sleeve. The drill sleeve is constructed of a radiolucent material that does not cast an image on the X-ray monitor. A drill bit connected to a surgical drill is then inserted through the drill sleeve. The drill bit is constructed of a radiopaque material that, like the trocar tip, creates a solid circular image on the X-ray monitor when the longitudinal axis of the drill bit is aligned parallel to the X-ray beam. That image can be used to ensure the proper alignment of the drill bit with the nail hole. Once the drill bit is properly aligned, the drill bit is drilled through the nail hole and the surrounding bone material.

After the drill bit is drilled through the first nail hole, the bit is detached from the drill and left in place in the bone. The aiming guide and protection sleeve are removed and rotated, so that the proximal end of the drill bit, which is extending out of the bone, can be inserted through a small hole located in the handle of the aiming guide. The axis of that small hole is parallel to that of the larger threaded hole that secures the protection sleeve. The distance between the axes of the large and small holes in the handle is the same as the distance between the two holes in the distal end of the nail. Thus, when the handle is reversed and the drill bit inserted into the smaller hole, the protection sleeve, which is located in the larger hole, is essentially aligned with the second hole in the nail. The concentric circular images cast by the protection sleeve and trocar on the X-ray monitor can then be used, as before, to ensure the proper alignment of the aiming guide with the second nail hole.

The protection sleeve and trocar are used, as before, to remove the soft tissue over the second nail hole. The trocar is then replaced with a drill sleeve and a second drill bit. The second drill bit is drilled accurately through the second nail hole and the surrounding bone material in the manner described above. The second drill bit and the drill sleeve are removed, and a locking screw is inserted through the protection sleeve and screwed through the bone and second nail hole to secure the nail to the bone. The aiming guide and protection sleeve are then repositioned over the first drill bit, which is still located in the bone and nail. The first drill bit is removed, and a second locking screw is inserted through the sleeve and screwed through the bone and first nail hole to secure the nail to the bone.

BRIEF DESCRIPTION OF DRAWINGS

Preferred features of the present invention are disclosed in the accompanying drawings, wherein similar reference characters denote similar elements throughout the several views, and wherein:

FIG. 1 shows a side view of the handle of the radiolucent aiming guide;

FIG. 2 shows a side view of a typical protection sleeve;

FIG. 3 shows a side view of a typical trocar;

FIG. 4 shows a side view of a typical drill sleeve;

FIG. 5 shows a side view of a typical drill bit;

DETAILED DESCRIPTION OF THE PREFERRED EMBODIMENT

Figure 6:
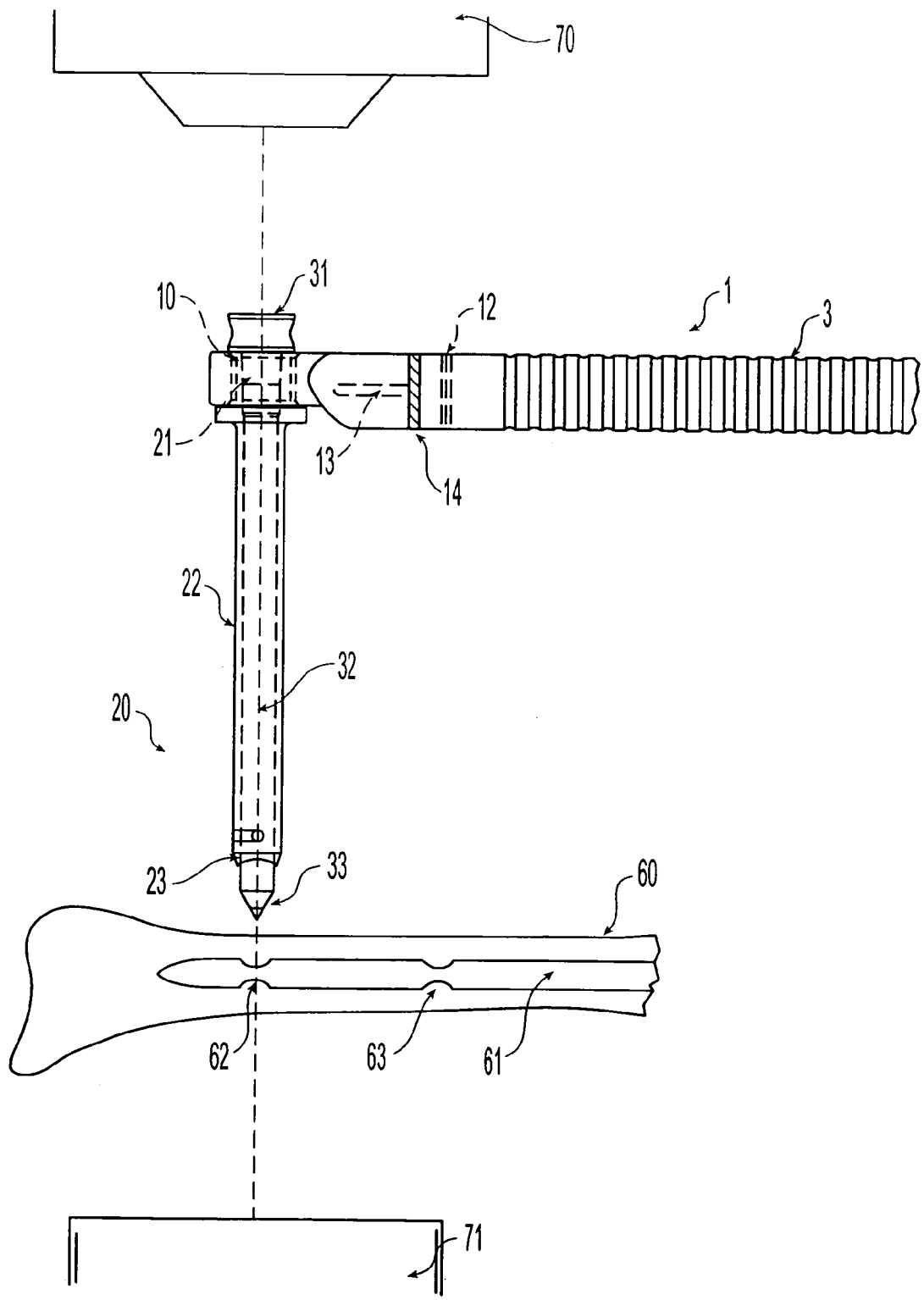
FIG. 6 shows an assembly of the handle, protection sleeve, and trocar, as they would be used to align the aiming guide with the first hole in the distal end of the intramedullary nail and to remove the soft tissue lying above the area of said first nail hole.

Referring to FIGS. 1–5, the radiolucent aiming guide is comprised of five major components—the handle 1, the protection sleeve 20, the trocar 30, the drill sleeve 40, and the drill bit 50. The construction of each of those components and the manner in which they are used are described below.

As shown in FIG. 1, the handle 1 of the aiming guide is an elongate member that is constructed substantially of a radiolucent material, such as plastic, which does not create an image on an X-ray monitor 71 when exposed to X-rays. The largest component of the handle 1 is the grip portion 3, into which are formed grooves 2 to improve the surgeon's hold on the aiming guide during surgery. The elongate shape of the handle 1 places the surgeon's hands at a safe distance away from the area that is exposed to X-rays.

In the preferred embodiment, end portions 4 and 11 are attached to the ends of the grip portion 3. The end portions 4 and 11 are almost identical in design, with the exception that the holes 8 and 12 are of different diameters in order to accommodate drill bits of different sizes. To help distinguish between the two sizes, the end portions 4 and 11 are connected to colored washers 14 and 15, respectively. The colored washers 14 and 15 are color-coded with the type of screw to be inserted. The end portions 4 and 11 are also oriented at 90 degrees with respect to each other about the longitudinal axis of the handle 1.

In an exemplary embodiment, end portion 4 and colored washer 15 are attached to the grip portion 3 by means of a male portion 5, which passes through the colored washer 15 and fits into a matching recess in the grip portion 3. A pin 6 is used to secure end portion 4 to grip portion 3. A similar arrangement (not shown in FIG. 1) is used to attach end portion 11 and colored washer 14 to grip portion 3.

Figure 7:
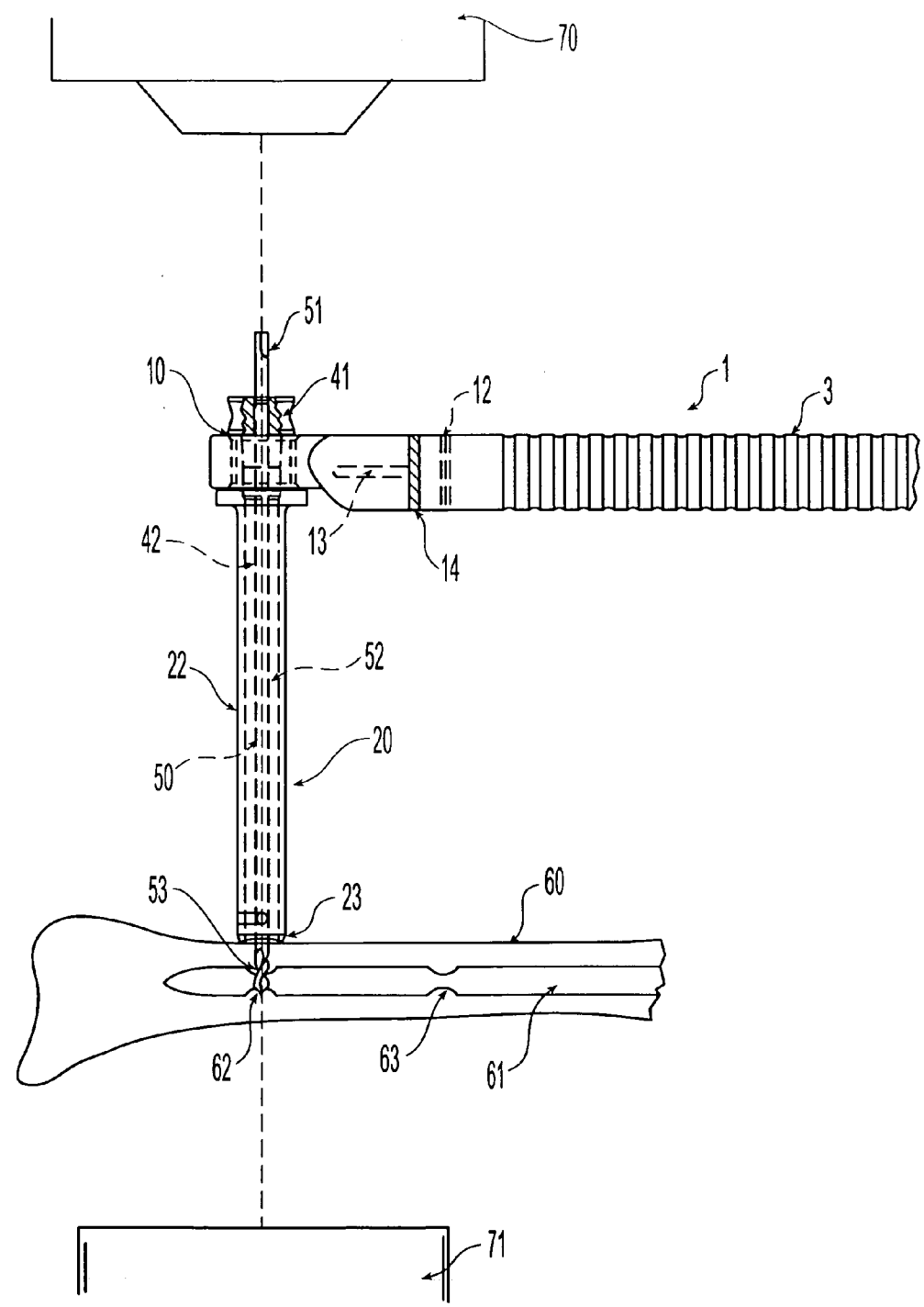
FIG. 7 shows an assembly of the handle, protection sleeve, drill sleeve, and drill bit, as they would be used to align the aiming guide with the first hole in the distal end of the intramedullary nail and to drill through said first nail hole.

A threaded hole 9 passes through end portion 4, perpendicular to the longitudinal axis of the grip portion 3. Threaded hole 9 is designed to engage the threaded head 21 of the protection sleeve 20, shown in FIG. 2. A second threaded hole 10 likewise passes through end portion 11, albeit perpendicular to both the longitudinal axis of the grip portion 3 and the axis of the first threaded hole 9. FIGS. 6 and 7 show a side view of the protection sleeve 20 fitted into the threaded hole 10 of end portion 11.

Figure 8:
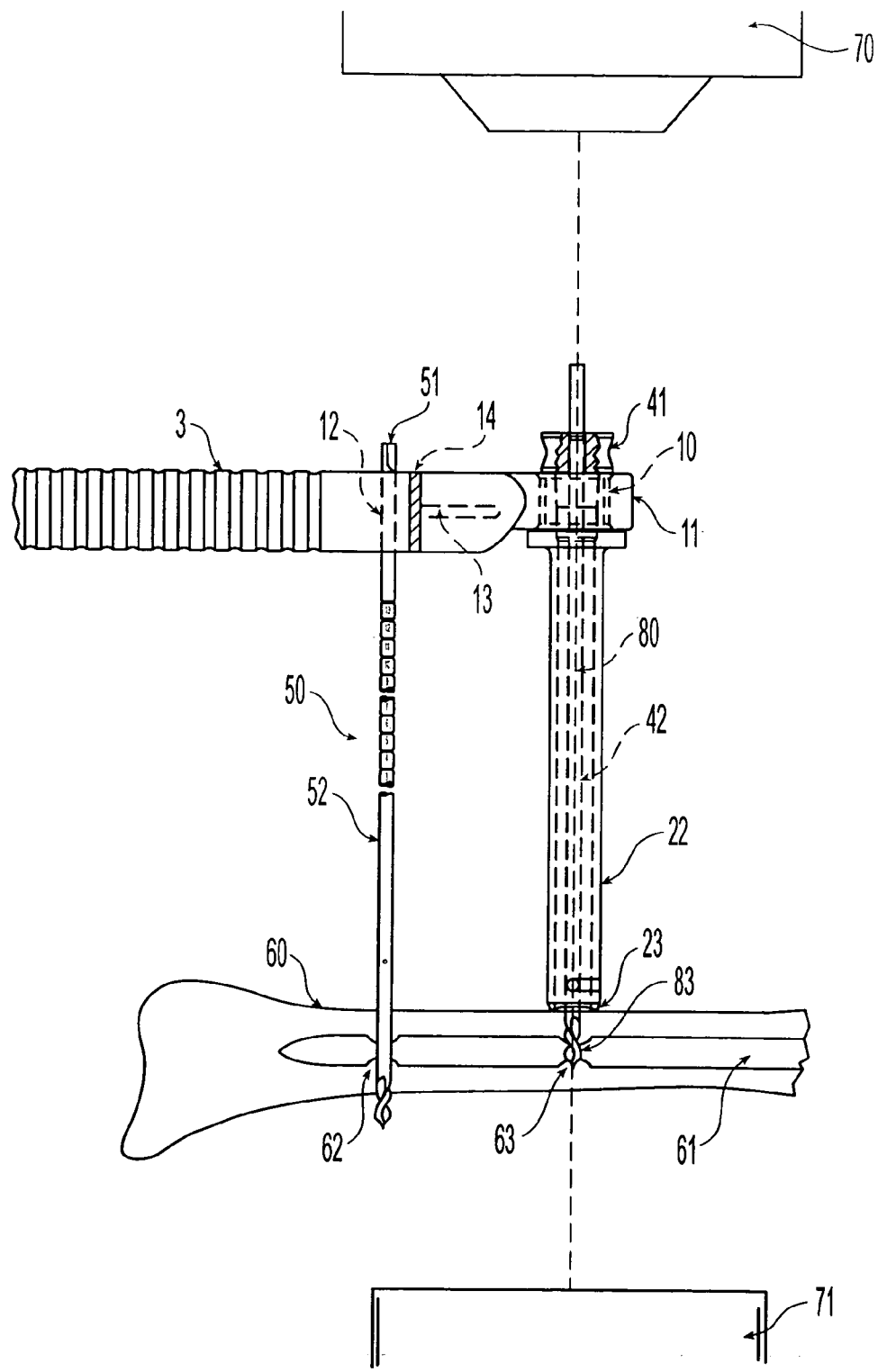
FIG. 8 shows an assembly of the handle, protection sleeve, drill sleeve, and drill bit, as they would be used to align the aiming guide with the second hole in the nail and to drill through said second nail hole.

Also passing through end portion 4 is a second, smaller hole 8. The axis of hole 8 is parallel to that of the larger, threaded hole 9. The diameter of hole 8 is sized so that it can receive the proximal end 51 of drill bit 50. A similar hole 12 passes through the end portion 11, parallel to the longitudinal axis of the threaded hole 10. However, hole 12 has a different diameter than hole 8 in order to accept a drill bit 50 with a different diameter. As shown in FIGS. 6–8, the distance between the axes of holes 10 and 12, as well as the distance between the axes of holes 8 and 9, is equal to the distance between the holes 62 and 63 in the distal end of the intramedullary nail 61. That design facilitates the location of the second hole 63 in the nail 61 after a drill bit 50 has been successfully drilled through the first hole 62 in the nail 61.

End portion 4 also contains a pair of elongate pins 7, which are constructed of metal or another radiopaque material. Pins 7 are parallel to the longitudinal axis of the handle 1, and lie on either side of and equidistant from that longitudinal axis. The plane on which pins 7 rest is perpendicular to the axis of the threaded hole 9. A similar pair of radiopaque pins 13 is located in end portion 11. Pins 13, like pins 7, are parallel to the longitudinal axis of handle 1 and lie on either side of and equidistant from that longitudinal axis. The plane on which both pins 13 rest is perpendicular to the longitudinal axis of the threaded hole 10 in end portion 11. As described in more detail below, the radiopaque pins 7 or 13 are used to help ensure the proper rotational alignment of the aiming guide with respect to the hole 62 or 63 in the intramedullary nail 61, shown in FIGS. 6–8.

FIG. 2 shows the protection sleeve 20. The protection sleeve 20 has a hollow cylindrical shaft portion 22 with a threaded head 21 for engagement with the threaded hole 9 or 10 in the handle 1. As shown in FIGS. 6–8, the longitudinal axis of the protection sleeve 20 is perpendicular to that of the handle 1 when the protection sleeve 20 is fitted into the threaded hole 9 or 10. Whereas protection sleeves used in the art are constructed entirely or substantially of metal, a radiopaque material, the present protection sleeve 20 is constructed substantially of a radiolucent material, with the exception of the tip 23 at its distal end, which is constructed of metal or another radiopaque material. The tip 23 has a roughened surface that can dig into the surface of the bone and thereby help prevent the aiming guide from slipping off the bone. When the longitudinal axis of the protection sleeve 20 is aligned parallel to the X-ray beam from the X-ray source 70, the radiopaque tip 23 will cast a dark circular image on the X-ray monitor 71. That dark circular image is used to align the aiming guide with the nail hole, described in more detail below. The present protection sleeve 20 is lighter in weight and does not obstruct the image on the X-ray monitor 71 to the same degree as the all-metal protection sleeves used in earlier aiming guides. Protection sleeves 20 may be made of various lengths in order to accommodate the varying thickness of the soft tissue.

The protection sleeve 20 is used in conjunction with the trocar 30, shown in FIG. 3. The trocar 30 has a solid, cylindrical shaft portion 32, which is sized to fit within the hollow cylindrical portion 22 of the protection sleeve 20. At the proximal end of the trocar 30 is a head portion 31, which rests above the top of the protection sleeve 20. Like the protection sleeve 20, the trocar 30 is constructed substantially of a radiolucent material, with the exception of the pointed tip 33 at its distal end, which is constructed of metal or another radiopaque material. In contrast, trocars previously used in the art were constructed entirely or substantially of metal, and thus were heavier and tended to obstruct the image on the X-ray monitor 71 to a greater degree than the present invention.

When the longitudinal axes of the trocar 30 and protection sleeve 20 are aligned parallel to the X-ray beam from X-ray source 70, the radiopaque tip 33 of the trocar and the radiopaque tip 23 of the protection sleeve will cast dark concentric circular images. Those concentric circular images are used to align the trocar 30 and protection sleeve 20 with the hole 62 or 63 in the nail 61. The surgeon will know the alignment is proper when the concentric circular images cast by the tips 23 and 33 of the protection sleeve and trocar, respectively, are superimposed over the circular image of the nail hole. The trocar 30 is used to aid in inserting the protection sleeve 20 through the soft tissue to the bone and to ensure that soft tissue does not enter the hollow inner portion of the protection sleeve 20.

The fourth major component of the aiming guide is the drill sleeve 40, which is shown in FIG. 4. The drill sleeve 40 is sized to fit within the protection sleeve 20 after the trocar 30 is removed. The drill sleeve 40 has a hollow, cylindrical shaft portion 42 and a head portion 41 at its proximal end. The drill sleeve 40 is constructed of a radiolucent material that does not cast an image on the X-ray monitor 71.

Finally, the aiming guide is used in conjunction with a drill bit 50. The shank 52 of the drill bit 50 is slightly smaller than the inner bore of the cylindrical shaft portion 42 of the drill sleeve 40. The drill bit 52 is constructed of metal, a radiopaque material, and thus casts a small dark circular image on the X-ray monitor 71 when its longitudinal axis is aligned parallel to the direction of the X-ray beam from X-ray source 70. The smaller holes 8 and 12 in the end portions 4 and 11, respectively, are sized to receive the head 51 of the drill bit 50 in the manner described below.

The aiming guide is used in the following fashion. A surgeon inserts the nail 61 into the medullary canal of the bone 60 across the area of the fracture. The X-ray source 70 and X-ray monitor 71 are positioned on either side of the area of the fracture. In particular, the X-ray source 70 is positioned so that hole 62 appears as a circle on the X-ray monitor 71, which indicates that the X-ray beam is parallel to the axis of hole 62. The part of the limb to be nailed is covered by a sterile radiation shield (not shown), except for the area directly above the distal holes in the intramedullary nail, which is left exposed. A scalpel or scissors (not shown) is then positioned over the nail hole 62 so that the X-ray monitor 71 shows the image cast by the tip of the scalpel to fall within the image of the hole 62 of the intramedullary nail 61. An incision is then made over the first nail hole 62. The process is repeated to make an incision over the second nail hole 63.

As shown in FIG. 6, the aiming guide is assembled by screwing the head 21 of the protection sleeve 22 into the threaded hole 9 or 10 of the handle portion 1. The trocar 30 is then inserted into the protection sleeve 20 so that the tip 33 of the trocar 30 extends slightly beyond the end 23 of the protection sleeve 20. When the axes of the protection sleeve 20 and trocar 30 are aligned with the direction of the X-ray beam from the X-ray source 70, their radiopaque tips 23 and 33, respectively, will form dark concentric circles on the monitor. The aiming guide is then moved until the concentric circular images cast by the tips 23 and 33 are centered on the image of the nail hole 62. The protection sleeve 20 and trocar 30 are then pressed into the incision above the nail hole 62 and through the soft tissue until they contact the cortex of the bone above the hole 62. The trocar 30 is used to remove the soft tissue lying above the hole 62. To prevent accidental lateral displacement of the aiming guide, the aiming guide is pressed firmly against the bone 60 so that the tip 23 of the protection sleeve 20 digs slightly into the surface of the bone 60.

The rotational alignment of the aiming guide can be checked by viewing the images cast by the pair of radiopaque pins 13 in the end portion 11 (or the pair of radiopaque pins 7, if end portion 4 is used instead). If the aiming guide is slightly rotated about the tip 23 of the protection sleeve 20, the distance between the images of the pair of radiopaque pins 13 will appear to expand or contract on the X-ray converter 71, as the protection sleeve 20 is brought into or out of alignment with the X-ray beam. When the images cast by the radiopaque pins 13 appear to lie on either side of and equidistant from the image of the nail 61, the surgeon will know that the longitudinal axes of the protection sleeve 20 and trocar 30 are properly aligned with the X-ray beam and thus with the nail hole 62.

After the protection sleeve 20 and trocar 30 are properly aligned with the nail hole 62 and the soft tissue above the nail hole 62 is removed, the trocar 30 is withdrawn from the protection sleeve 20 and replaced with the drill sleeve 40. The drill bit 50 is then inserted through the drill sleeve 40, as shown in FIG. 7. When the axes of the protection sleeve 20 and drill bit 50 are properly aligned with the X-ray beam and the nail hole 62, the radiopaque tip 23 of the protection sleeve 20 and the drill bit 50 will cast dark concentric circular images over the image of the nail hole 62 on the X-ray converter 71. The drill bit 50 is then used to drill accurately through the nail hole 62 and surrounding bone material.

After the drill bit 50 is drilled through the nail hole 62, the head 51 of the drill bit 50 is disconnected from the power drill (not shown), and the aiming guide, including the protection sleeve 20 and drill sleeve 40, is lifted up, leaving drill bit 50 in place in the bone 60 and nail 61. The drill sleeve 40 is removed from the protection sleeve 20 and replaced with the trocar 30. As shown in FIG. 8, the aiming guide is then turned 180 degrees about the longitudinal axis of the protection sleeve 20, and the head portion 51 of the drill bit 50 is inserted through the small hole 12 in end portion 11 (or through the small hole 8, if end portion 4 is being used instead). The distance between the axes of the threaded hole 10 and the small hole 12 in end portion 11 (like the distance between small hole 8 and threaded hole 9 in end portion 4) is equal to the distance between the nail holes 62 and 63. Thus, by reversing the handle 1 and inserting the head 51 of the drill bit 50 into the small hole 12, the protection sleeve 20 and trocar 30 are automatically closely aligned with the second hole 63 of the nail 61. The protection sleeve 20 and trocar 30 can then be precisely aligned with the nail hole 63 using the X-ray images of their radiopaque tips 23 and 33, respectively, in the manner described above. The trocar is used to remove the soft tissue above the nail hole 63, after which the trocar 30 is removed and replaced by the drill sleeve 40 and a second drill bit 80 having a drill tip 83. The concentric circular images cast by the second drill bit 80 and the radiopaque tip 23 of protection sleeve 20 are then used to precisely align the second drill bit 80 with the nail hole 63, in the same manner as described above. The second drill bit 80 is then accurately drilled through the second nail hole 63 and the surrounding bone material 60. The second drill bit 80 and drill sleeve 40 are removed, and a locking screw (not shown) is inserted through the protection sleeve 20 and screwed through the bone 60 and second nail hole 63 to secure the nail 61 to the bone 60. The aiming guide and protection sleeve 20 are then repositioned over the first drill bit 50, which is still located in the bone 60. The first drill bit 50 is then removed, and a second locking screw (not shown) is inserted through the protection sleeve 20 and screwed through the bone 60 and the first nail hole 62 to secure the nail 61 to the bone 60.

While the various descriptions above relate to a particular embodiment of the invention, it should be understood that the various features can be used singly or in any combination thereof. Therefore, this invention is not to be limited to the specific preferred embodiment depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of using a radiolucent aiming guide for locating a hole in an implanted intramedullary nail and inserting a locking screw, said method comprising the steps of:
    inserting the intramedullary nail, having at least one nail hole, into a medullary canal of a bone;
    positioning an imaging source and imaging monitor such that the imaging source is parallel to an axis of the intramedullary nail hole;
    inserting a trocar, having a longitudinal axis and a radiopaque tip at a distal end, into a protection sleeve of the radiolucent aiming guide, the radiolucent aiming guide including a pair of radiopaque pins disposed within a handle of the radiolucent aiming guide;
    aligning the axes of the protection sleeve and the trocar with the imaging source;
    replacing the trocar from the protection sleeve with a drill sleeve;
    inserting a drill bit through the drill sleeve and aligning the axes of the protection sleeve and drill bit with the imaging source and the intramedullary nail hole;
    accurately drilling through the intramedullary nail hole and surrounding bone material;
    removing the drill bit and drill sleeve; and
    inserting the locking screw through the protection sleeve and screwing the locking screw through the bone material and nail hole to secure the intramedullary nail to the bone.

2. A method of using a radiolucent aiming guide according to claim 1, wherein the imaging source is positioned parallel to the axis of the intradmedullary nail hole when the intramedullary nail hole appears as a circle on the imaging monitor.

3. A method of using a radiolucent aiming guide according to claim 2, wherein the protection sleeve, having a proximal end and a distal end, comprises:
    a substantially cylindrical, hollow body constructed substantially of a radiolucent material and having a longitudinal axis;
    a head at the proximal end of the hollow body for engaging the radiolucent aiming guide, the head being constructed substantially of a radiolucent material; and
    a tip at the distal end of the hollow body, the tip being constructed of a radiopaque material so that the tip will cast a substantially circular image on an X-ray monitor when an incident beam from the imaging source is aligned parallel to the longitudinal axis of the hollow body.

4. A method of using a radiolucent aiming guide according to claim 3, wherein the axes of the protection sleeve and the trocar are aligned with the imaging source when the radiopaque tips of the protection sleeve and trocar form dark concentric circles on the imaging monitor.

5. A method of using a radiolucent aiming guide according to claim 4, further comprising the step of moving the radiolucent aiming guide until the dark concentric circles cast by the radiopaque tips of the protection sleeve and trocar are centered on the image of the intramedullary nail.

6. A method of using a radiolucent aiming guide according to claim 5, further comprising the steps of:
    pressing the protection sleeve and trocar against the bone material above the intramedullary nail hole;
    using the trocar to remove soft tissue lying above the bone material above the intramedullary nail hole; and
    embedding the tip of the protection sleeve into the surface of the bone material so as to prevent lateral displacement.

7. A method of using a radiolucent aiming guide according to claim 6, wherein proper alignment of the longitudinal axes of the protection sleeve and trocar with the imaging source is determined when images of the radiopaque pins appear to lie on either side of and equidistant from the image of the intramedullary nail.

8. A method of using a radiolucent aiming guide according to claim 1, wherein the trocar has a substantially cylindrical body constructed substantially of a radiolucent material.

9. A method of using a radiolucent aiming guide for locating a hole in an implanted intramedullary nail and inserting a locking screw, said method comprising the steps of:

inserting the intramedullary nail, having at least one nail hole, into a medullary canal of a bone;

positioning an imaging source and imaging monitor such that the imaging source is parallel to an axis of the intramedullary nail hole;

inserting a trocar, having a longitudinal axis and a radiopaque tip at a distal end, into a protection sleeve of the radiolucent aiming guide, the radiolucent aiming guide comprising an elongated handle constructed substantially of a radiolucent material and having a longitudinal axis; the handle having a first hole for engaging a first protection sleeve, the axis of the first hole being perpendicular to the longitudinal axis of the handle; and a pair of radiopaque pins disposed within the handle, the pins lying on both sides of and parallel to the longitudinal axis of the handle and lying in a plane perpendicular to the axis of the first hole;

aligning the axes of the protection sleeve and the trocar with the imaging source;

replacing the trocar from the protection sleeve with a drill sleeve;

inserting a drill bit through the drill sleeve and aligning the axes of the protection sleeve and drill bit with the imaging source and the intramedullary nail hole;

accurately drilling through the intramedullary nail hole and surrounding bone material;

removing the drill bit and drill sleeve; and inserting the locking screw through the protection sleeve and screwing the locking screw through the bone material and nail hole to secure the intramedullary nail to the bone.

\* \* \* \* \*